United States Patent
Senaratne (10) Patent No.: US 9,193,947 B2
(45) Date of Patent: *Nov. 24, 2015

(54) PROCESS FOR CULTURING MICROORGANISMS ON A SELECTED SUBSTRATE

(71) Applicant: INEOS BIO S.A., Lisle, IL (US)

(72) Inventor: Ryan Senaratne, Fayetteville, AR (US)

(73) Assignee: INEOS BIO SA, Rolle (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/892,482

(22) Filed: May 13, 2013

(65) Prior Publication Data

US 2013/0316435 A1    Nov. 28, 2013

Related U.S. Application Data

(60) Provisional application No. 61/650,098, filed on May 22, 2012, provisional application No. 61/650,093, filed on May 22, 2012, provisional application No. 61/650,077, filed on May 22, 2012, provisional application No. 61/650,084, filed on May 22, 2012.

(51) Int. Cl.
| | |
|---|---|
| C12N 3/00 | (2006.01) |
| C12P 7/06 | (2006.01) |
| C12R 1/01 | (2006.01) |
| C12R 1/145 | (2006.01) |
| C12N 1/20 | (2006.01) |
| B01D 53/62 | (2006.01) |
| C12P 7/08 | (2006.01) |

(52) U.S. Cl.
CPC ........ *C12N 3/00* (2013.01); *B01D 53/62* (2013.01); *C12N 1/20* (2013.01); *C12P 7/065* (2013.01); *C12P 7/08* (2013.01); *C12R 1/01* (2013.01); *C12R 1/145* (2013.01); *Y02E 50/17* (2013.01)

(58) Field of Classification Search
CPC ........ C02F 3/28; C02F 3/2806; C02F 3/2813; C12N 1/22; C12N 3/00; C12N 1/20; C12P 1/00; C12P 5/00; C12P 7/06; C12P 7/065; C12R 1/01; C12R 1/145; C12R 1/025; Y02E 10/00; Y02E 50/10

See application file for complete search history.

(56) References Cited

U.S. PATENT DOCUMENTS

| | | | |
|---|---|---|---|
| 5,173,429 | A | 12/1992 | Gaddy et al. |
| 5,593,886 | A | 1/1997 | Gaddy |
| 5,807,722 | A | 9/1998 | Gaddy |
| 5,972,661 | A | 10/1999 | Kubera |
| 6,136,577 | A | 10/2000 | Gaddy |
| 7,285,402 | B2 | 10/2007 | Gaddy |
| 2003/0211585 | A1 | 11/2003 | Gaddy et al. |
| 2007/0275447 | A1 | 11/2007 | Lewis |
| 2010/0227377 | A1 | 9/2010 | Adams |
| 2011/0229947 | A1* | 9/2011 | Zahn et al. ............ 435/161 |
| 2013/0005014 | A1* | 1/2013 | Bell et al. ............ 435/168 |

FOREIGN PATENT DOCUMENTS

| | | |
|---|---|---|
| WO | WO 98/00558 | 1/1998 |
| WO | WO 00/68407 | 11/2000 |
| WO | WO 2007/117157 | 10/2007 |
| WO | WO 2009/022925 | 2/2009 |
| WO | WO 2009/064200 | 5/2009 |
| WO | 2009114127 | 9/2009 |
| WO | WO 2009/113878 | 9/2009 |

OTHER PUBLICATIONS

Hitzman, D.O. et al. 1956. Requirements for Production and Germination of Spores of Anaerobic Bacteria. Anaerobic Spore Germination 47: 1-7. specif. pp. 1-3, 6-7.*
Long, S. et al. 1983. Sporulation of Clostridium acetobutylicum P262 in a Defined Medium. Applied and Environmental Microbiology 45(4): 1389-1393. specif. pp. 1389-1390.*
The Physics Factbook (Mass of a Bacterium. Datasheet [online]. Louis Siu (2003) [retrieved on Feb. 26, 2014]. Retrieved from the Internet: <URL: http://hypertextbook.com/facts/2003/LouisSiu.shtml> p. 1.*
Bahl, H. et al. 1986. Nutritional Factors affecting the Ratio of Solvents Produced by Clostridium acetobutylicum. Applied and Environmental Microbiology 52(1): 169-172. specif. pp. 169-170.*
LabTools (Bacterial cell No. (OD600). Datasheet [online]. LabTools. Copyright 2014 [retrieved on Feb. 28, 2014]. Retrieved from the Internet: <URL: http://www.labtools.us/bacterial-cell-number-od600> p. 1.*
O'Brien R.W. et al. 1971. Oxygen and the Growth and Metabolism of Clostridium acetobutylicum. Journal of General Microbiology 68: 307-318. specif. p. 308.*
Ramachandriya, K.D. et al. 2010. Heat Shocking of Clostridium Strain P11 to Promote Sporulation and Ethanol Production. Biological Engineering 2(2): 115-131. specif. p. 117.*
Maedeh, Mohammadi et al., "Bioconversion of Synthesis Gas to Second Generation Biofuels:" A Review, Renewable and Sustainable Energy Reviews; 15; Sep. 15, 2011, pp. 4255-4273.
Saxena, Jyotisna et al., "Effect of Trace Metals on Ethanol Production from Synthesis Gas . . . "; J Ind. Microbiol Biotechnol; Apr. 2011; 38 (4); 513-21.
Tiraado-Acevedo et al., "Influence of Carbon Source Pre-Adaptation on Clostridium ljungdahlii Growth and Product Formation," Bioprocessing & Biotechniques, Oct. 24, 2011, pp. 1-5.
Cotter, Jacqueline et al.; "Ethanol and acetate production by Clostridium ljungdahlii and Clostridium autoethanogenum using resting cells" Bioprocess Biosyst; 2009; 32:369-80.
Duc, Le et al. "Germination of the spore in the gastrointestinal tract provides a novel route for heterologous antigen delivery" Science Direct; Vaccine 21 (Jun. 21, 2003) 4215-24.
Heiskanen, Harri et al. "The effect of syngas composition on the growth and product formation of Butyribacterium methylotrophicum" Science Direct; Enzyme and Microbial.

(Continued)

*Primary Examiner* — John S Brusca
*Assistant Examiner* — Sharon M Papciak
(74) *Attorney, Agent, or Firm* — INEOS USA LLC (57) ABSTRACT

A process is provided that is effective for allowing bacteria to be cultured in a selected substrate. Bacteria are sporulated and then germinated in the presence of a selected substrate and medium.

5 Claims, 7 Drawing Sheets

(56) References Cited

OTHER PUBLICATIONS

Technology 41 (Mar. 8, 2007) 362-367.
Irigul, O. et al. "Sporulation-specific expression of the yvW (cadA) gene and the effect of blockage on spore properties in Bacillus subtilis" Gene 382 (2006) 71-8.
Setlow, Peter; "Spore germination" Current Opinion in Microbiology; 2003, 6:550-566.
Webb, Martin et al. Historical and Contemporary NaCl Concentrations Affect the Duration and Distribution of Lag Times from Individual Spores of Nonproteolytic Clostridium botulinum; Appl. environ. Microbio; Feb. 2, 2007; 73(7): 2118-2127. DOI: 10.1128/AEM.01744-06.
International Search Report and Written Opinion of the International Searching Authority regarding PCT/US2013/041105 dated Sep. 5, 2013 (12 pgs.).
K. Thomas Klasson, et al, Bioconversion of synthesis gas into liquid or gaseous fuels, Enzyme Microb. Technol., 1992, vol. 14, 7 pages.
International Searching Authority, International Search Report and Written Opinion issued in PCT/US2013/041029, mailed Sep. 5, 2013, 13 pages.
BD Biosciences, BD Bionutrients Technical Manual Advanced Bioprocessing, Third Edition Revised, Oct. 2006, 72 pages.

* cited by examiner

PROCESS FOR CULTURING MICROORGANISMS ON A SELECTED SUBSTRATE

This application claims the benefit of U.S. Provisional Application Nos. 61/650,098, 61/650,093, 61/650,077 and 61/650,084, all filed on May 22, 2012, all of which are incorporated in their entirety herein by reference.

A process is provided that is effective for allowing bacteria to be cultured in a selected substrate. More specifically, bacteria are sporulated and then germinated in the presence of a selected substrate and medium.

BACKGROUND

Acetogenic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

Many acetogenic microorganisms are poorly suited for industrial scale bioprocessing and have therefore not demonstrated commercial viability for this purpose. Such microorganisms have slow doubling time and low total productivities. In addition, many techniques for genetic manipulation (knockout, over-expression of transgenes via integration or episomic plasmid propagation) are inefficient, time-consuming, laborious, or non-existent.

Acetogenic microorganisms may be grown to produce ethanol from carbon monoxide. The growth process may involve culturing the acetogenic bacteria on increasing amounts of CO over time. There exists a need to more quickly develop microorganisms and methods of their use to utilize syngas or other gaseous carbon sources for the production of desired chemicals and fuels.

SUMMARY

A process for culturing bacteria in a selected substrate includes reducing an amount of a first substrate to convert at least a portion of the bacteria to spores. The process further includes adding the selected substrate to the spores and germinating at least a portion of the spores in the selected substrate.

In another aspect, a process for culturing bacteria to grow on a production medium includes replacing at least a portion of a first medium with the production medium to convert at least a portion of the bacteria to spores. The process further includes germinating at least a portion of the spores in the production medium.

In another aspect, a process for culturing bacteria on syngas includes replacing at least a portion of a first substrate with syngas and replacing at least a portion of a first medium with a production medium to convert at least a portion of the bacteria to spores. The process further includes germinating the spores in the production medium with syngas.

BRIEF DESCRIPTION OF FIGURES

The above and other aspects, features and advantages of several aspects of the process will be more apparent from the following figures.

DETAILED DESCRIPTION

The following description is not to be taken in a limiting sense, but is made merely for the purpose of describing the general principles of exemplary embodiments. The scope of the invention should be determined with reference to the claims.

The processes described herein are effective for providing a fermentation with a high level of ethanol productivity. In this aspect, the process is effective for providing a specific STY (specific space time yield expressed as g ethanol/(L·day·gram cells) of at least about 1, in another aspect, about 1 to about 10, in another aspect, about 2 to about 8, in another aspect, about 3 to about 7, and in another aspect, about 4 to about 6.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "cell recycle" refers to separation of microbial cells from a fermentation broth and returning all or part of those separated microbial cells back to the fermentor. Generally, a filtration device is used to accomplish separations.

Acetogenic Culture

In one aspect, the process includes culturing or propagating bacteria in a first medium that may include a first substrate. The first medium may provide bacteria with suitable carbon and energy sources and other nutrients, including growth factors. In this aspect, the first medium includes components such vitamins, trace elements, and amino acids. The first medium may include carbon sources including yeast extract, carbohydrates, alcohol, amino acids, peptone, peptides, protein, fatty acids, lipid and mixtures thereof. For example, bacteria supplied from culture collections such as ATCC, may include recommended mediums that include components such as peptone, glucose, fructose, yeast extract, amino acids, vitamins and trace elements. The first medium may provide components that allow for a rapid increase in cell density. In this aspect, the first medium may have a pH of about 5.7 to about 7.0. Some examples of a first medium that may be utilized include ATCC medium 1754, ATCC medium 1136 (with yeast extract 0.1%, sodium acetate 50 mM and methanol 100 mM, ATCC Medium 1019 and ATCC Medium 1016.

In another aspect, the first medium and substrate are effective for maintaining a cell density of about 0.005 g/L or more, in another aspect, about 0.02 g/L or more, in another aspect, about 0.03 g/L or more, in another aspect, about 0.04 g/L or more, in another aspect, about 0.05 g/L or more, in another aspect, about 0.1 g/L or more, in another aspect, about 0.3 g/l or more, in another aspect, about 0.5 g/L or more, in another aspect, about 0.75 g/L or more, and in another aspect, about 1.0 g/L or more.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* 0-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfbtomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

Sporulation

Upon establishing a bacteria in a first medium and first substrate, the amount of the first substrate is reduced. Concentrations of components in the first medium may also be reduced along with the first substrate. In this aspect, the first medium may be replaced with a production medium. In other aspects, the first substrate and the selected substrate may be the same or they may be different.

In one aspect, the first medium and first substrate may be replaced up to a maximum rate equal to a maximum rate of a pump employed to supply the production medium. In another aspect, bacteria may be concentrated from the first medium, such as for example in the form of a pellet, and transferred directly into a production medium In another aspect, prior to sporulation, a carbon source may be added to maintain a cell density of about 0.005 g/L or more, in another aspect, about 0.02 g/L or more, in another aspect, about 0.03 g/L or more, in another aspect, about 0.04 g/L or more, in another aspect, about 0.05 g/L or more, in another aspect, about 0.1 g/L or more, in another aspect, about 0.3 g/l or more, in another aspect, about 0.5 g/L or more, in another aspect, about 0.75 g/L or more, and in another aspect, about 1.0 g/L or more. Some examples of carbon sources that may be added include yeast extract, alcohol, carbohydrates, amino acids, peptone, peptides, protein, fatty acids, lipids and mixtures thereof.

Reducing input of a first substrate is effective for causing at least a portion of the bacteria to sporulate. Spores are formed by intracellular division within the cytoplasm of a mother cell. Spore-forming bacteria initiate sporulation in response to adverse environmental changes, such as nutrient limitation. After being formed, the mature spores are released from the mother cells (for additional details see Brun, et al. eds. *Prokaryotic Development*. Endospore-forming bacteria: an overview, ed. A. L. Sonenshein. 2000, American Society for Microbiology: Washington, D.C. 133-150; Cutting, S., ed. *Molecular Biology Methods for Bacillus*. Sporulation, germination and outgrowth, ed. W. L. Nicholson and P. Setlow. 1990, John Wiley and Sons: Sussex, England. 391-450 which are incorporated herein by reference). Spores are generally oval or spherical in shape and are wider than vegetative bacterial cells. Other distinctive spore forms include spindle-shaped, club-shaped forms, and tennis racket-shaped structures.

In this aspect, a first substrate is reduced in an amount effective for providing a spore number to cell number ratio of at least about 0.05, in another aspect a spore number to cell number ratio of at least about 0.1, and in another aspect a spore number to cell number ratio of at least about 0.5. Spores may be quantified using known methods, such as for example, visual inspection and counting using a hemocytometer.

Germination

In accordance with the process, a select substrate in a production medium is added to the bacteria spores. Addition of a selected substrate is effective for causing spores to germinate. As a spore proceeds through germination towards cell division, there are various stages, including (1) spore activation; (2) stage I germination, during which water partially rehydrates the spore core; (3) stage II germination, during which cortex hydrolysis occurs and metabolism resumes; and (4) outgrowth, during which cell division occurs (for additional details see Setlow, P., *Spore germination. Curr Opin Microbiol,* 2003. 6: p. 550-556; Foster, S. J. et al. *Pulling the trigger: the mechanism of bacterial sporegermination. Mol Microbiol,* 1990. 4: p. 137-141; and Moir, et al., *Spore germination. Cell Mol Life Sci,* 2002. 59: p. 403-409, each of which are incorporated herein by reference).

In accordance with the process, germination is effective for providing a spore to cell number ratio of at least about 0.04, in another aspect a spore to cell number ratio of at least about 0.01, and in another aspect a spore to cell number ratio of at least about 0.001. In an aspect where the selected substrate is CO, the process is effective for providing a specific CO uptake of at least about 0.25 mmole/min/gram of cells, in another aspect, at least about 0.50 mmole/min/gram of cells, in another aspect, at least about 0.75 mmole/min/gram of cells, and in another aspect, at least about 1.0 mmole/min/gram of cells.

Production mediums are those that contain a lower concentration of nutrients for growth. The production medium may contain a carbon source for bacterial growth, various salts, which may vary among bacteria species and growing conditions; these generally provide essential elements such as magnesium, nitrogen, phosphorus, and sulfur to allow the bacteria to synthesize protein and nucleic acids. The production medium may have a pH of about 5 to about 4.1. In one aspect, the sole carbon provided by the production medium is provided by syngas. One example of production medium is as follows:

| Component | Concentration Range (expressed as mg or μg nutrient per gram of cells) | Preferred Range (expressed as mg or μg nutrient per gram of cells) |
| --- | --- | --- |
| nitrogen (N) | 112-160 mg | 140-150 mg |
| phosphorus (P) | 10.5-15 mg | 12-13 mg |
| potassium (K) | 26-36 mg | 28-33 mg |
| iron (Fe) | 2.7-5 mg | 3.0-4.0 mg |
| tungsten (W) | 10-30 μg | 15-25 μg |
| Nickel (Ni) | 34-40 μg | 35-37 μg |
| Cobalt (Co) | 9-30 μg | 15-20 μg |
| Magnesium (Mg) | 4.5-10 mg | 5-7 mg |
| Sulfur (S) | 11-20 mg | 12-16 mg |
| Thiamine | 6.5-20 μg | 7-12 μg |

In one aspect, the medium includes one or more of a nitrogen source, a phosphorous source and a potassium source. The medium may include any one of the three, any combination of the three, and in an important aspect, includes all three. A nitrogen source may include a nitrogen source selected from the group consisting of ammonium chloride, ammonium phosphate, ammonium sulfate, ammonium nitrate, and mixtures thereof. A phosphorous source may include a phosphorous source selected from the group consisting of phosphoric acid, ammonium phosphate, potassium phosphate, and mixtures thereof. A potassium source may include a potassium source selected from the group consisting of potassium chloride, potassium phosphate, potassium nitrate, potassium sulfate, and mixtures thereof.

In one aspect, the medium includes one or more of iron, tungsten, nickel, cobalt, magnesium, sulfur and thiamine. The medium may include any one of these components, any combination, and in an important aspect, includes all of these components. An iron may include an iron source selected from the group consisting of ferrous chloride, ferrous sulfate, and mixtures thereof. A tungsten source may include a tungsten source selected from the group consisting of sodium tungstate, calcium tungstate, potassium tungstate, and mixtures thereof. A nickel source may include a nickel source selected from the group consisting of nickel chloride, nickel sulfate, nickel nitrate, and mixtures thereof. A cobalt source may include a cobalt source selected from the group consisting of cobalt chloride, cobalt fluoride, cobalt bromide, cobalt iodide and mixtures thereof. A magnesium source may include a magnesium source selected from the group consisting of magnesium chloride, magnesium sulfate, magnesium phosphate, and mixtures thereof. A sulfur source may include cysteine, sodium sulfide, and mixtures thereof.

In one aspect, a production medium will include a carbon source that is provided only by the selected substrate, such as for example CO. In this aspect, the production medium may have less than about 0.01 g/L of a carbon source other than carbon provided by the selected substrate. Examples of other added carbons may include yeast extract, alcohol, peptides, protein, fatty acid, lipid and mixtures thereof.

Syngas

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The syngas will have a $CO/CO_2$ ratio of at least about 0.75. Some examples of suitable gasification methods and apparatus are provided in U.S. Ser. Nos. 13/427,144, 13/427,193 and 13/427,247, all of which were filed on Apr. 6, 2011, and all of which are incorporated herein by reference.

In another aspect, syngas utilized for propagating acetogenic bacteria may be substantially CO. As used herein, "substantially CO" means at least about 50 mole % CO, in another aspect, at least about 60 mole % CO, in another aspect, at least about 70 mole % CO, in another aspect, at least about 80 mole % CO, and in another aspect, at least about 90 mole % CO.

Bioreactor Operation

In accordance with one aspect, the fermentation process is started by addition of medium to the reactor vessel. The medium is sterilized to remove undesirable microorganisms and the reactor is inoculated with the desired microorganisms.

Upon inoculation, an initial feed gas supply rate is established effective for supplying the initial population of microorganisms. Effluent gas is analyzed to determine the content of the effluent gas. Results of gas analysis are used to control feed gas rates. Upon reaching desired levels, liquid phase and cellular material is withdrawn from the reactor and replenished with medium.

EXAMPLES

Example 1

Growth of *Butyribacterium methylotrophicum* on Syngas after Culturing on Methanol and Lowering the pH Inoculum Preparation:
*Butyribacterium methylotrophicum* was grown in serum bottles (13 bottles with 25 ml each) in BM medium. The BM medium had the following composition:

| Compound | ml/L |
|---|---|
| 1) distilled water | 807 |
| 2) mineral solution #1 | 50 |
| 3) mineral solution #2 | 25 |
| 4) 8% Na2Co3 solution | 50 |
| 5) Wolfe's Mineral solution | 10 |
| 6) Resazurin (1 g/L) | 1 |
| 7) Yeast extract | 1 |
| 8) Sodium acetate (3M) | 17 |
| After autoclave: | |
| 9) Wolfe's Vitamin solution | 10 |
| 10) Cysteine-sulfide reducing agent | 20 |
| 11) Methanol (100%) | 10 |

Wolfe's Mineral solution is available from ATCC (Trace Mineral Supplement, catalog number MD-TMS).
Wolfe's Vitamin solution is available from ATCC (Vitamin Supplement, catalog number MD-VS).
Mixing Protocol:
Mix #1 through #8, autoclave, cool under $N_2$
Transfer to anaerobic chamber, add #9 through #11 (anaerobic and sterile)
Adjust to pH 7.2
Bioreactor Operation:
A bioreactor was inoculated with 325 ml of *Butyribacterium methylotrophicum* grown as described above. Methanol was added to the bioreactor (92.5 mL/L) at the start to increase the original cell density (0.049 g/L) of the culture. Growth medium was gradually replaced with a production medium (low pH minimal medium with syngas as the sole carbon source) as described below.
Media Change Events

| Time (Hours) | Media change event |
|---|---|
| 149 | 10 ml methanol/L to media bottle |
| 191 | changed media bottle to 5 ml methanol/L |
| 214 | added 10 ml/L ATCC trace metals to media bottle |
| 335 | changed media bottle to 2.5 ml methanol/L visual evaluation of culture |
| 359 | changed media bottle to production medium with no methanol |
| 383 | visual evaluation of culture |
| 360 | added 5 ml methanol to the reactor added 20 ml MPFN/L to media bottle |
| 407 | added 14.7 ml ATCC vitamin/L to media bottle visual evaluation of culture |
| 480 | visual evaluation of culture |

Change of Growth Medium Flow Rates to the Reactor

| Process Time (hours) | Change of flow rate per liter to the reactor | |
|---|---|---|
| 76.30 | 0.28 ml/min | BM medium |
| 119.33 | 0.38 ml/min | BM medium |
| 171.50 | 0.00 ml/min | BM medium |
| 196.50 | 0.28 ml/min | BM medium |
| 335.42 | 0.53 ml/min | BM medium |
| 359.83 | 0.46 ml/min | production medium |
| 461.67 | 0.63 ml/min | production medium |

Production Medium
(preparation of which is described in U.S. Pat. No. 7,285,402 which is incorporated herein by reference)

| Component | Quantity per liter |
|---|---|
| 2 g/L $FeCl_2 \cdot 4H_2O$ | 10 ml |
| 85% $H_3PO_4$ | 0.05 ml |
| MPFN Trace metals | 20 ml |
| $(NH_4)_2HPO_4$ | 0.6 g |
| $NH_4Cl$ | 2.0 g |
| NaCl | 0.2 g |
| KCl | 0.15 g |
| $MgCl_2 \cdot 6H_2O$ | 0.5 g |
| $CaCl_2 \cdot 2H_2O$ | 0.2 g |
| Cysteine | 0.25 g |

As shown above, methanol in the bioreactor was reduced by 50% twice and then removed completely over a 15 day period. MPFN (which contains Ni) was added two days after removal of methanol from the medium.
Results:
Visual observations provided the following indications:

| Time (Hours) | Spore to cell ratio |
|---|---|
| 335 | 1:1 |
| 383 | 5.7:1 |
| 407 | 9.75:1 |
| 480 | 0.23:1 |

Figure 1:
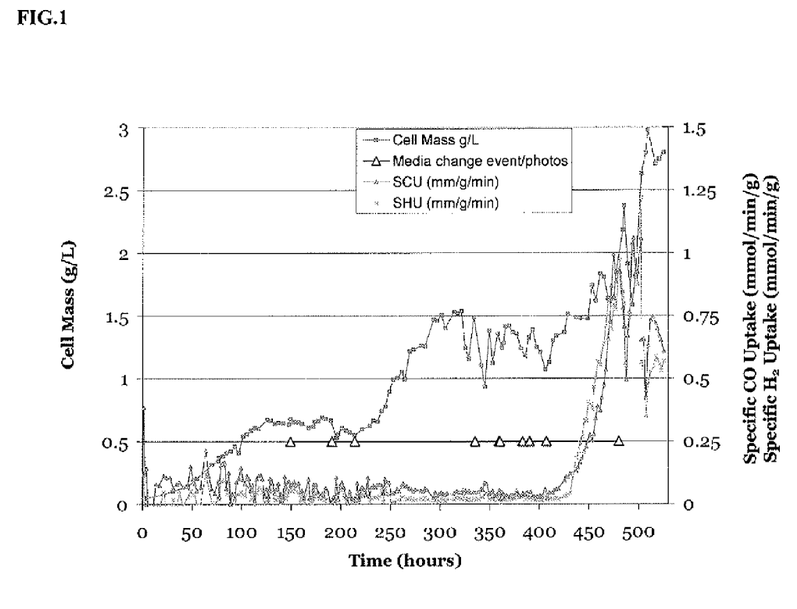
FIG. 1 illustrates growth of *Butyribacterium methylotrophicum* on syngas through sporulation and germination after culturing on methanol and lowering the pH.

Culture parameters including cell mass, specific CO uptake and specific $H_2$ uptake were monitored. As illustrated in FIG. 1, specific CO and specific $H_2$ uptake began to increase at about 450 hours.

Example 2

Reactor Start-Up with Frozen *Butyribacterium methylotrophicum* Previously Grown on Syngas Six hundred milliliters of frozen *Butyribacterium methylotrophicum* harvested from Example 1 was inoculated into 1400 ml of production medium. Starting cell density was 0.39 g/L. CO consumption was monitored and was above 0.4 mmole/min/g within the first 24 hours.

Example 3

Growth of *Butyribacterium methylotrophicum* on Syngas after Culturing on Yeast Extract, Methanol and Acidification Inoculum Preparation:
*Butyribacterium methylotrophicum* was grown in serum bottles in a medium that included yeast extract and had a pH of 7.2-7.4. The medium is described in Heiskanen et al.

(2007) Enzyme and Microbial Technology, Vol. 41, Issue 3, pages 362-367, which is incorporated herein by reference.

Bioreactor Operation:

A bioreactor that contained one liter of medium as described above was inoculated with 100 ml of *Butyribacterium methylotrophicum* grown as described above. Starting cell density was 0.04 g/L.

Yeast extract was added to the bioreactor to increase cell density according to the following protocol:

| Time (hours) | Volume added per liter in the reactor |
|---|---|
| 85.38 hr | 2.5 ml |
| 89.08 hr | 2.5 ml |
| 113.73 hr | 3.75 ml |
| 330.58 hr | 3.77 ml |

Composition of the yeast extract: 20% in DI water

An acetic solution was added to the bioreactor to lower pH. Acetic solution and addition protocol were as follows:

Acetic Solution

| Compound | Amount |
|---|---|
| NaCl | 0.9 g/L |
| $MgCl_2 \cdot 6H_2O$ | 0.2 g/L |
| $CaCl_2 \cdot 2H_2O$ | 0.1 g/L |
| $NH_4Cl$ | 1.0 g/L |
| yeast extract | 0.5 g/L |
| Trace minerals solution | 10 ml/L |
| Resazurin | 2 ml/L |
| Acetic Acid | 80.0 ml/L |

Acetic Solution Addition Protocol

| Time (hours) | Volume added per liter in the reactor |
|---|---|
| 66.82 | 11.25 ml |
| 84.22 | 6.25 ml |
| 89.50 | 7.5 ml |

Methanol (26.92 ml of a 10% solution) was added at 253.8 hours to increase cell density. Growth medium was gradually replaced with a production medium (low pH minimal medium with syngas as the sole carbon source) as described below.

Change of Growth Medium Flow Rates to the Reactor

| Time (hours) | Change of flow rate of minimal medium per L to the reactor |
|---|---|
| 109.00 | 0.63 ml/min |
| 226.67 | 0.00 ml/min |
| 402.08 | 0.20 ml/min |
| 419.00 | 0.42 ml/min |
| 425.40 | 0.59 ml/min |
| 443.73 | 0.77 ml/min |

Results:

Visual observations provided the following indications:

| Time (Hours) | Spore to cell ratio |
|---|---|
| 36 | 0.15:1 |
| 60 | 0.75:1 |
| 84 | 1.25:1 |
| 108 | 1.29:1 |
| 132 | 1.23:1 |

Figure 2:
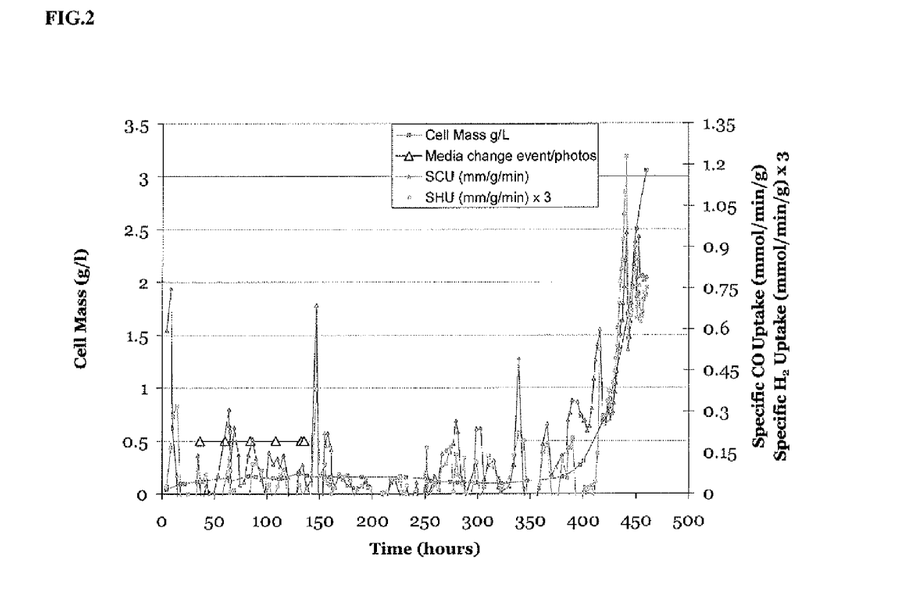
FIG. 2 illustrates growth of *Butyribacterium methylotrophicum* on syngas through sporulation and germination after culturing on yeast extract, methanol and acidification.

Culture parameters including cell mass, specific CO uptake and specific $H_2$ uptake were monitored. As illustrated in FIG. 2, specific CO and specific $H_2$ uptake began to increase at about 450 hours.

Example 4

Growth of *Butyribacterium methylotrophicum* on Syngas after Culturing on Yeast Extract and Acidification Inoculum Preparation:

*Butyribacterium methylotrophicum* was grown in serum bottles in medium as described in Example 3.

Bioreactor Operation:

A bioreactor was inoculated with 350 ml of *Butyribacterium methylotrophicum* grown as described above. The above 350 ml of *Butyribacterium methylotrophicum* inoculum was transferred into a 1250 ml of growth medium containing yeast extract. Composition of the initial growth medium in the reactor was as follows:

Initial Growth Medium

| Component | Amount |
|---|---|
| mineral salt stock solution | 12.5 ml/L |
| ATCC trace mineral supplement | 10.0 ml/L |
| ATCC vitamin supplement | 10.0 ml/L |
| reducing agent | 10.0 ml/L |
| cysteine | 0.45 g/L |
| yeast extract | 0.1% |

Mineral salt solution: (80 g/L NaCl, 100 g/L $NH_4Cl$, 10 g/L KCl, 10 g/L $KH_2PO_4$, g/L $MgSO_4 \cdot 7H_2O$, 4 g/L $CaCl_2$-$H_2O$)

There was no measureable syngas consumption by the culture after the inoculation. As a way of increasing the cell density of the culture yeast extract was added to the reactor at time points indicated below. The pH of the reactor was gradually changed to 4.7 by adding an acetic solution (described above) to the reactor as indicated in the table below. Also medium in the reactor was gradually exchanged into the desired production medium (described above) as indicated in the table below.

Addition of Yeast Extract to Increase the Initial Cell Mass in the Reactor:

| Time (hours) | Volume added per liter in the reactor |
|---|---|
| 47.25 | 4.12 ml |
| 91.25 | 4.67 ml |
| 122.35 | 4.17 ml |

Composition of the yeast extract: 20% in DI water.

Addition of Acetic Solution to Lower the pH in the Reactor:

| Time (hours) | Volume added per liter in the reactor |
| --- | --- |
| 117.25 | 13.33 ml |
| 118.42 | 20.00 ml |
| 120.25 | 32.26 ml |
| 120.97 | 31.25 ml |
| 121.25 | 30.30 ml |

Exchange of Medium in the Reactor with Low pH, Production Medium with No Yeast Extract:

| Time (hours) | Change of flow rate of minimal medium to the bioreactor |
| --- | --- |
| 122.63 | 0.18 ml/min |
| 161.75 | 40 ml of medium added directly to the bioreactor |
| 163.28 | 0.32 ml/min |
| 168.28 | 0.65 ml/min |
| 225.25 | 0.00 ml/min |
| 427.00 | 0.59 ml/min |
| 428.38 | 1.18 ml/min |
| 433.87 | 0.00 ml/min |
| 576.97 | 0.16 ml/min |
| 625.33 | 0.50 ml/min |
| 625.88 | 0.58 ml/min |

Results:

Visual observations provided the following indications:

| Time (Hours) | Spore to cell ratio |
| --- | --- |
| 163 | 043:1 |
| 499 | 3.4:1 |
| 571 | 5.4:1 |
| 595 | 0.45:1 |
| 619 | 0.27:1 |

Figure 3:
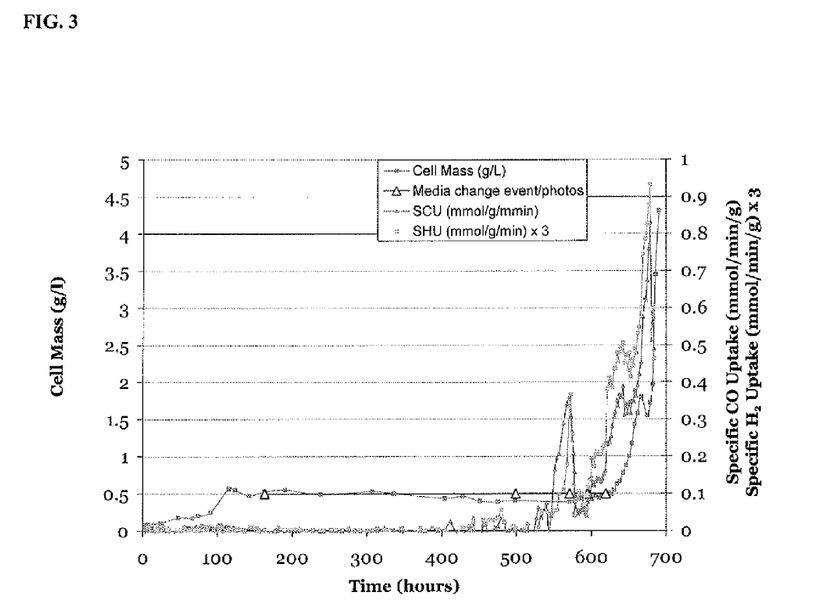
FIG. 3 illustrates growth of *Butyribacterium methylotrophicum* on syngas after culturing on yeast extract and acidification.

Culture parameters including cell mass, specific CO uptake and specific $H_2$ uptake were monitored. As illustrated in FIG. 3, specific CO and specific $H_2$ uptake began to increase at about 600 hours.

Example 5

Inoculation of a Bioreactor Containing Low pH Production Medium with *Butyribacterium methylotrophicum* Previously Grown on Syngas Bacteria from Example 4 were maintained in serum bottles in MES medium (without yeast extract or fructose) for 28 days. These serum bottles were regularly checked for head space gas composition and refilled with syngas when necessary.

The bioreactor was inoculated with 210 ml of *Butyribacterium methylotrophicum* grown in above serum bottles. The 210 ml of *Butyribacterium methylotrophicum* was transferred into 1 liter of production medium (as described herein) containing no yeast extract or any organic carbon substrate. The initial cell density and the pH of the culture after the inoculation were 0.03 g/L and 4.7 respectively.

Production Medium Flow Rates to the Reactor

| Time (hours) | Change of flow rate of minimal medium to the reactor |
| --- | --- |
| 122 | 0.5 ml/min |
| 144 | 1.0 ml/min |
| 152 | 2.0 ml/min |

Results:

Visual observations provided the following indications:

| Time (Hours) | Spore to cell ratio |
| --- | --- |
| 2 | 0.37:1 |
| 26 | 0.04:1 |
| 50 | 0.06:1 |
| 74 | 0.23:1 |

Figure 4:
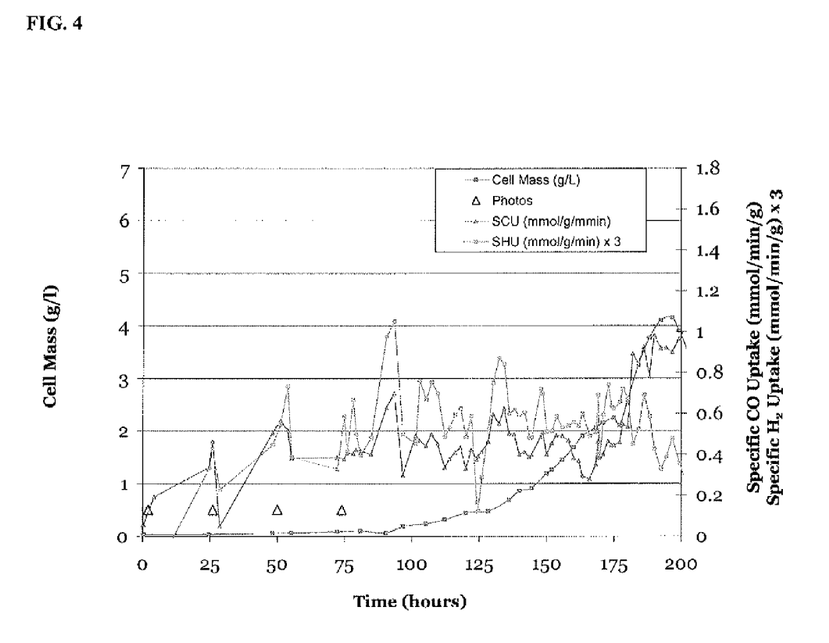
FIG. 4 illustrates growth of *Butyribacterium methylotrophicum* on syngas after previously growing *Butyribacterium methylotrophicum* on syngas.

Culture parameters including cell mass, specific CO uptake and specific $H_2$ uptake were monitored and are shown in FIG. 4.

Example 6

Adaptation of *Clostridium autoethanogenum* Through Sporulation and Germination to Utilize Syngas in a Low pH Medium (without Yeast Extract)

Inoculum Preparation:

An inoculum of *Clostridium autoethanogenum* was prepared as follows:

Inoculum Growth Medium

| Component | Amount |
| --- | --- |
| MES buffer | 10 g/L |
| mineral salt stock solution | 12.5 ml/L |
| ATCC trace mineral supplement | 10.0 ml/L |
| ATCC vitamin supplement | 10.0 ml/L |
| Fructose | 10.0 g/L |
| yeast extract | 1.0 g/L |
| resazurin | 0.01 g/L |

Mineral salt solution: (80 g/L NaCl, 100 g/L $NH_4Cl$, 10 g/L KCl, 10 g/L $KH_2PO_4$, 20 g/L $MgSO_4.7H_2O$, 4 g/L $CaCl_2.H_2O$)

Bioreator Operation:

A bioreactor was inoculated with *Clostridium autoethanogenum* grown in the medium described above containing yeast extract and fructose. The initial pH of the culture in the reactor was 4.7 and the cell density was 0.03 g/L. There was no measureable syngas consumption by the culture after the inoculation.

There were no cell density increases in first 20 hours after inoculation. Fructose and yeast extract were added to reactor as indicated below to make conditions less unfavorable and also as a way of increasing initial cell density of the culture. Additionally reactor was inoculated with bacteria three more times as indicated below. The above additional inoculations were done to further increase the initial cell density of the reactor. Throughout the experiment as indicated below, medium in the reactor was gradually exchanged into a production medium (as described herein). During this process bacteria in the reactor sporulated and germinated into a culture that can utilize syngas in a low pH minimal medium without yeast extract and fructose. Redox of the culture in the reactor was maintained below −140 my by adding one of the two reducing agents described below.

Addition of Yeast Extract to Increase the Initial Cell Mass in the Reactor:

| Process Time (hours) | Volume added per liter in the reactor or media bottle | |
|---|---|---|
| 168 | 5.0 ml | To reactor and media |
| 216 | 10.0 ml | To media |
| 284 | 5.0 ml | To media |

Composition of the yeast extract: 20% in DI water

Addition of Fructose to Increase the Initial Cell Mass in the Reactor:

| Process Time (hours) | Volume added per liter in the reactor or to the media bottle | |
|---|---|---|
| 20 | 12.5 ml | To reactor |
| 23 | 12.5 ml | To reactor |
| 24 | 12.5 ml | To reactor |
| 25 | 12.5 ml | To reactor |
| 216 | 10.0 ml | To media bottle |
| 310 | 10.3 ml | To reactor |
| 311 | 32.4 ml | To reactor |
| 312 | 10.8 ml | To reactor |
| 329 | 10.8 ml | To reactor |
| 330 | 21.6 ml | To reactor |
| 337 | 32.4 ml | To reactor |
| 353 | 22.2 ml | To reactor |
| 362 | 10.5 ml | To reactor |
| 368 | 10.5 ml | To reactor |

Composition of fructose: 25% in DI water

Additional Inoculation of the Reactor with *Clostridium autoethanogenum* Grown in a Rich Medium:

| Process (hours) | Volume added per liter in reactor |
|---|---|
| 47 | 36 ml |
| 168 | 163 ml |
| 187 | 29 ml |

Compositions of Reducing Agents Used in the Experiment:
9 g/L NaOH, 40 g/L L-cysteine, 40 g/L $Na_2S$, $H_2O$, $TiCl_3$ (Sigma Aldrich 14010).

Exchange of Medium in the Reactor from Initial Growth Medium to Production Medium:

| Process Time (hours) | Change of flow rate of minimal medium to the reactor, volume added per liter and media type | |
|---|---|---|
| 30.5 | 0.49 ml/min | Initial minimal growth medium |
| 161 | 0.0 ml/min | Initial minimal growth medium |
| 216 | 0.28 ml/min | Initial minimal growth medium |
| 284 | 0.51 ml/min | Initial minimal growth medium |
| 407 | 0.53 ml/min | Final minimal growth medium |

Results:
Visual observations provided the following indications:

| Time (Hours) | Spore to cell ratio |
|---|---|
| 187 | 0.58:1 |
| 210 | 0.83:1 |
| 234 | 1.07:1 |
| 282 | 0.18:1 |
| 306 | 0.25:1 |
| 330 | 0.16:1 |

Figure 5:
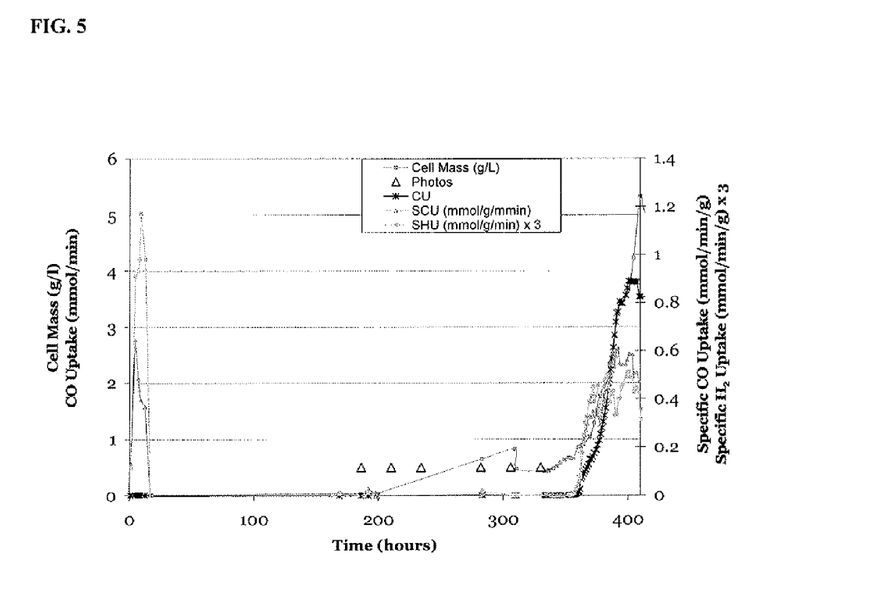
FIG. 5 illustrates growth of *Clostridium autoethanogenum* on syngas after culturing on yeast extract and lowering the pH.

Culture parameters including cell mass, specific CO uptake and specific $H_2$ uptake were monitored and are illustrated in FIG. 5.

Example 7

Adaptation of *Clostridium ljungdahli* PETC Through Sporulation and Germination to Utilize Syngas in a Low pH Medium (without Yeast Extract)

Inoculum Preparation:
*Clostridium ljungdahli* PETC inoculum was first grown in a medium of pH 5.7 containing (0.1%) yeast extract and (1%) fructose as described below. Yeast extract and fructose in the above inoculum culture was diluted by transferring those cultures (160 ml) into the same growth medium (1000 ml) without yeast extract and fructose. After incubating this culture for 5 days at 37 C, 930 ml of this culture was transferred to a seed reactor containing 1200 ml of minimal medium as described below. After 16 days of incubation, 200 ml of this seed culture was transferred to another reactor containing 1200 ml of the same above minimal medium. The initial pH of the culture in the reactor was 5.4 and the initial cell density was 0.05 g/L.

Media Used to Grow the Inoculum Bacteria:

| Component | Amount |
|---|---|
| MES | 10 g/L |
| mineral salt stock solution | 12.5 ml/L |
| ATCC trace mineral supplement | 10.0 ml/L |
| ATCC vitamin supplement | 10.0 ml/L |
| Reducing agent | 10.0 ml/L |
| resazurin | 0.01 g/L |

Mineral salt stock solution: (80 g/L NaCL, 100 g/L $NH_4Cl$, 10 g/L KCL, 10 g/L $KH_2PO_4$, 20 g/L $MgSO_4.7H_2O$, 4 g/L $CaCl_2.H_2O$)

Reducing Agent composition:
9 g/L NaOH, 40 g/L L-cysteine, 40 g/L $Na_2S$, 1 L $H_2O$.

Production Medium:
0.15 g/L KCl, 0.5 g/L $MgCl_2.6H_2O$, 0.2 $CaCl_2.2H_2O$, 2 g/L $NH_4Cl$, 0.6 g $(NH_4)_2HPO_4$, 0.2 g/L NaCl, 0.45 g/L Cysteine. 10 ml/L Trace Mineral Supplement: (100 ml/L 85% $H_3PO_4$, 0.3 g/L $MgSO_4.7H_2O$, 0.5 g/L $MnSO_4.H_2O$, 1.0 g/L NaCl, 0.1 g/L $FeSO_4.7H_2O$, 0.1 g/L $Co(NO_3)_2.6H_2O$, 0.1 g/L $CaCl_2$, 0.1 g/L $ZnSO_4.7H_2O$, 0.01 g/L $CuSO_4.5H_2O$, 0.02 g/L $AlK(SO_4)_2.12H_2O$, 0.01 g/L $H_3BO_3$, 0.01 g/L $Na_2MoO_4.2H_2O$, 0.001 g/L $Na_2SeO_3$, 0.01 g/L $Na_2WO_4.2H_2O$, 0.02 g/L $NiCl_2.6H_2O$). 10 ml/L vitamins (0.002 g/L folic acid, 0.01 g/L pyridoxine hydrochloride, 0.005 g/L Riboflavin, 0.026 g/L Biotin, 0.065 g/L Thiamin, 0.005 g/L Nicotinic acid, 0.0353 g/L Calcium Pantothenate, 0.0001 g/L Vitamin B12, 0.005 g/L p-Aminobenzoic acid, 0.005 Thiotic acid, 0.9 g/L Monopotassium phosphate).

Bioreactor Operation:
As a way of increasing the cell density of the culture, fructose was added to the reactor at time points indicated below. As shown below, the rate of (minimal) media flow to the reactor was gradually increased to provide nutrients to the culture, to dilute the fructose in the growth medium and also to lower the pH of the culture to 4.9 (from 5.4).

Addition of Fructose to Increase the Initial Cell Mass in the Reactor:

| Process Time (hours) | Volume added per liter in the reactor |
|---|---|
| 167 | 17.2 ml |
| 239 | 16.1 ml |
| 279 | 16.1 ml |
| 312 | 16.7 ml |
| 332 | 16.1 ml |
| 357 | 16.1 ml |

Composition of fructose: 20% in DI water
Production Medium Flow Rate to the Reactor:

| Process Time (hours) | Change of flow rate of production medium to the reactor |
|---|---|
| 50 | 0.21 ml/min. |
| 70 | 0.32 ml/min |
| 572 | 0.70 ml/min |

Results:
Visual observations provided the following indications:

| Time (Hours) | Spore to cell ratio |
|---|---|
| 19 | 0.38:1 |
| 43 | 0.71:1 |
| 67 | 0.94:1 |
| 139 | 0.6:1 |
| 307 | 2:1 |
| 379 | 0.8:1 |
| 475 | 0.36:1 |
| 571 | 0.05:1 |

Figure 6:
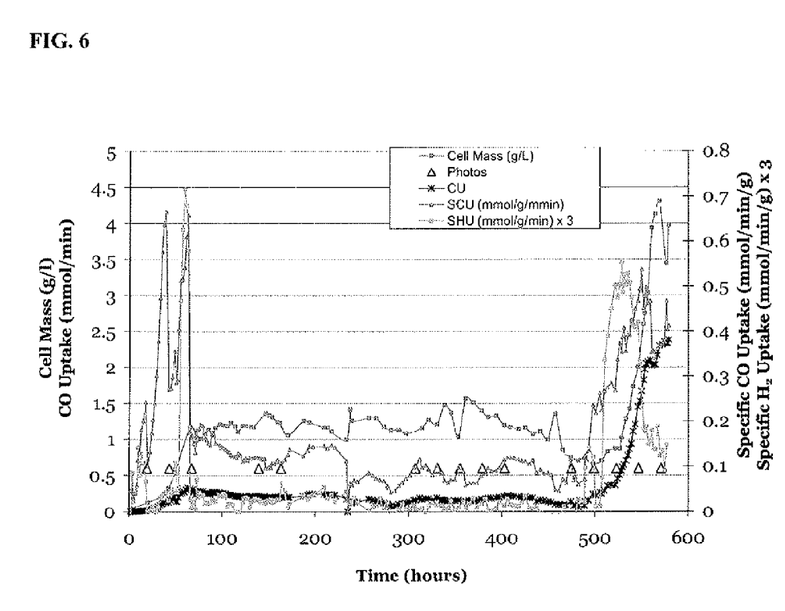
FIG. 6 illustrates growth of *Clostridium ljungdahlii* on syngas after culturing on yeast extract and lowering the pH.

Culture parameters including cell mass, specific CO uptake and specific $H_2$ uptake were monitored and are illustrated in FIG. 6.

Example 7

Reverse Adaptation of *Clostridium ljungdahli*

*Clostridium ljungdahli* were grown in serum bottles containing 30 ml of the below described growth medium (pH adjusted to 5.7) with or without fructose and with or without syngas. *C. ljungdahli* cultures were grown in a 37° C. shaking (60 rpm) incubator.

*C. ljungdahli* growing in the above growth medium using syngas as the carbon and energy source was transferred into a serum bottle (labeled fructose) containing the same growth medium but supplemented with 1% fructose. This serum bottle did not contain syngas. For comparison purposes *C. ljungdahli* using syngas as the carbon and energy source was also transferred into a serum bottle (labeled syngas) containing syngas and the growth medium (without fructose).

Figure 7:
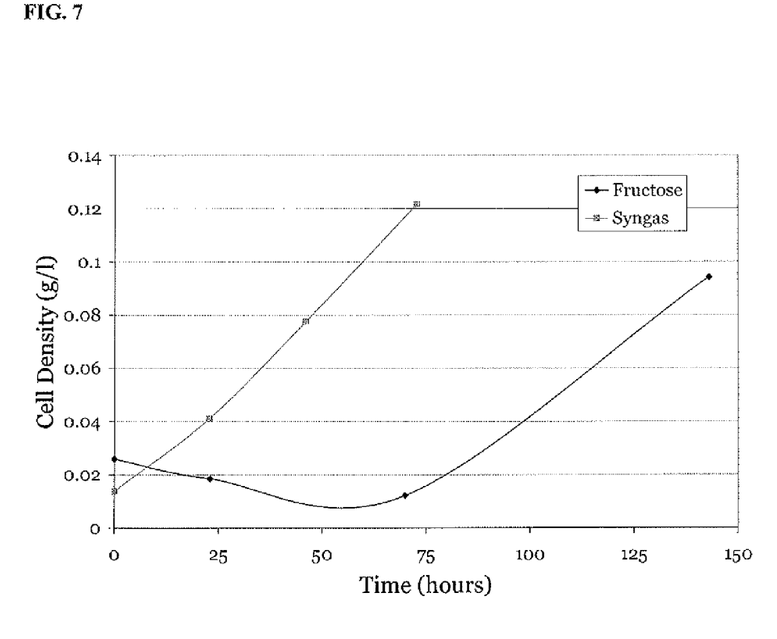
FIG. 7 illustrates growth of syngas fermenting *Clostridium ljungdahlii* on fructose.

As indicated in the below table and in FIG. 7, syngas fermenting *C. ljungdahli* transferred into fructose went through a cycle of sporulation and germination before they started growing using fructose as the energy and the carbon source.

Visual observations provided the following indications:

| Time (Hours) | Spore to cell ratio in fructose serum bottle |
|---|---|
| 0 | 1:0.15 |
| 23 | 1:1.63 |
| 70 | 1:0.7 |
| 143 | 1:0.1 |

| Time (Hours) | Spore to cell ratio in syngas serum bottle |
|---|---|
| 0 | 1:0.11 |
| 22.75 | 1:0.0625 |
| 46 | 1:0.14 |
| 72.75 | 1:0.12 |

Media used to grow the bacteria: 10 g/L MES, 12.5 ml/L Mineral Salt Stock Solution (80 g/L NaCL, 100 g/L $NH_4Cl$, 10 WL KCL, 10 g/L $KH_2PO_4$, 20 g/L $MgSO_4.7H_2O$, 4 g/L $CaCl_2.H_2O$), 10.0 ml/L ATCC Trace Mineral Supplement, 10.0 ml/L ATCC Vitamin Supplement, 10.0 ml/L Reducing Agent, 0.001 g/L resazurin.

Mineral salt Stock solution: (80 g/L NaCL, 100 g/L $NH_4Cl$, 10 g/L KCL, 10 g/L $KH_2PO_4$, 20 g/L $MgSO_4.7H_2O$, 4 g/L $CaCl_2.H_2O$)

Reducing Agent composition: 9 g/L NaOH, 40 g/L L-cysteine, 40 g/L $Na_2S$, $11H_2O$.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for culturing acetogenic bacteria on syngas, the process comprising:
   culturing the acetogenic bacteria on a first substrate to provide a cell density of at least about 0.005 g/L, wherein the first substrate includes a carbon source selected from the group consisting of yeast extract, carbohydrates, alcohol, amino acids, peptone, peptides, protein, fatty acids, lipid and mixtures thereof;
   sporulating the acetogenic bacteria by replacing at least a portion of the first substrate with syngas having at least about 10 mole % CO and replacing at least a portion of a first medium with a production medium to convert at least a portion of the bacteria to spores, wherein the sporulating provides a spore number to cell number ratio of about 0.05 or more; and
   germinating the spores in the production medium at a pH of about 4.1 to about 5 with syngas having at least about 10 mole % CO to provide a specific CO uptake of at least about 0.25 mmole/min/gram of cells and a space time yield (STY) of about 1 g or more ethanol/(L·day gram cells).

2. The process of claim 1 wherein the syngas has a $CO/CO_2$ molar ratio of at least about 0.75.

3. The process of claim 1 wherein the acetogenic bacterium is selected from the group consisting of *Acetogenium kivui*, *Acetoanaerobium noterae*, *Acetobacterium woodii*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany),

*Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui,* and mixtures thereof.

4. The process of claim 1 wherein germinating is effective for providing a spore number to cell number ratio of about 0.04 or less.

5. The process of claim 1 wherein the production medium comprises at least one or more of:
   at least about 112 mg of nitrogen per gram of cells,
   at least about 10.5 mg of phosphorous per gram of cells, or
   at least about 26 mg of potassium per gram of cells.

* * * * *